US008870845B2

(12) United States Patent (10) Patent No.: US 8,870,845 B2
Nakagawa et al. (45) Date of Patent: Oct. 28, 2014

(54) METHOD FOR ALLEVIATING CONDITION OF SPINAL CANAL STENOSIS BY LOCAL ADMINISTRATION OF MEDICINE

(75) Inventors: Yuji Nakagawa, Ashigarakami-gun (JP); Suguru Hata, Ashigarakami-gun (JP); Yuichi Tada, Ashigarakami-gun (JP); Yasushi Kinoshita, Ashigarakami-gun (JP)

(73) Assignee: Terumo Kabushiki Kaisha, Tokyo (JP)

( * ) Notice: Subject to any disclaimer, the term of this patent is extended or adjusted under 35 U.S.C. 154(b) by 71 days.

(21) Appl. No.: 13/370,846

(22) Filed: Feb. 10, 2012

(65) Prior Publication Data

US 2012/0209242 A1    Aug. 16, 2012

Related U.S. Application Data

(60) Provisional application No. 61/441,425, filed on Feb. 10, 2011.

(51) Int. Cl.
*A61M 31/00*    (2006.01)
*A61K 9/00*    (2006.01)
*A61B 17/00*    (2006.01)

(52) U.S. Cl.
CPC .................................. *A61K 9/0019* (2013.01)
USPC .......................................... 604/500; 424/400

(58) Field of Classification Search
None
See application file for complete search history.

(56) References Cited

U.S. PATENT DOCUMENTS

| | | | |
|---|---|---|---|
| 4,983,385 A | 1/1991 | Hasegawa et al. | |
| 6,325,796 B1 | 12/2001 | Berube et al. | |
| 6,962,586 B2 | 11/2005 | Berube et al. | |
| 8,357,388 B2 * | 1/2013 | McKay | 424/423 |
| 8,425,459 B2 * | 4/2013 | Wang | 604/103.02 |
| 2003/0073988 A1 | 4/2003 | Berube et al. | |
| 2004/0241094 A1 | 12/2004 | Chung et al. | |
| 2005/0249775 A1 * | 11/2005 | Falotico et al. | 424/423 |
| 2006/0116672 A1 | 6/2006 | Berube et al. | |
| 2009/0116711 A1 | 5/2009 | Larson et al. | |
| 2011/0020427 A1 | 1/2011 | Zhang et al. | |
| 2011/0125081 A1 | 5/2011 | Sen | |

FOREIGN PATENT DOCUMENTS

SU    1297822 A  *  3/1987

OTHER PUBLICATIONS

Collins English Dictionary, "Proximity", © HarperCollins Publishers 2003, <http://www.thefreedictionary.com/proximity>, p. 1-4.*
Staats et al., "Lumbar Stenosis Complicating Retained Epidural Catheter Tip", Anesthesiology, vol. 83, No. 5, Nov. 1995, pp. 1115-1118.
Konno et al., "Effects of OP-1206 (Prostaglandin $E_1$) on Nerve-Conduction Velocity in the Dog Cauda Equina Subjected to Acute Experimental Compression", Journal of Spinal Disorders, vol. 9, No. 2, 1996 (month unknown), pp. 103-106.
Nakai et al., "The Effects of OP-1206 α-CD on Walking Dysfunction in the Rat Neuropathic Intermittent Claudication Model", Anesth Analg 2002; 94, (month unknown), pp. 1537-1541.
Matsudaira et al., "The Efficacy of Prostaglandin E1 Derivative in Patients With Lumbar Spinal Stenosis", Spine, vol. 34, No. 2, 2009 (month unknown) pp. 115-120.
Yaksi et al., "The Efficiency of Gabapentin Therapy in Patients With Lumnbar Spinal Stenosis", Spine, vol. 32, No. 9, 2007 (month unknown), pp. 939-942.
Shirasaka et al. "Vasodilative Effects of Prostaglandin $E_1$ Derivate on Arteries of Nerve Roots in a Canine Model of a Chronically Compressed Cauda Equina", BMC Musculoskeletal Disorders, 2008 (month unknown), 9:41, pp. 1-7.
Liadó et al., "A Prognostic Index of the Survival of Patients With Unresectable Hepatocellular Carcinoma After Transchatheter Arterial Chemoembolization", Cancer, Jan. 1, 2000, vol. 88, No. 1, pp. 50-57.
Chan et al., "A Prospective Study Regarding the Complications of Transcatheter Intraarterial Lipiodol Chemoembolization in Patients With Hepatocellular Carcinoma", Cancer, Mar. 15, 2002, vol. 94, No. 6, pp. 1747-1752.
Song et al., "Association Between Insulin-Like Growth Factor-2 and Metastases After Transcatheter Arterial Chemoembolization in Patients With Hepatocellular Carcinoma", Cancer, Jun. 15, 2001, vol. 91, No. 12, pp. 2386-2393.
Koda et al., "Combination Therapy With Transcatheter Arterial Chemoembolization and Percutaneous Ethanol Injection Compared With Percutaneous Ethanol Injection Alone for Patients With Small Hepatocellular Carcinoma", Cancer, Sep. 15, 2001, vol. 92, No. 6, pp. 1516-1524.
Seki et al., "Combination Therapy With Transcatheter Arterial Chemoembolization and Percutaneous Microwave Coagulation Therapy for Hepatocellular Carcinoma", Cancer, Sep. 15, 2000, vol. 89, No. 6, pp. 1245-1251.
Hsieh et al., "Comparison of Transcatheter Arterial Chemoembolization, Laparoscopic Radiofrequency Abalation, and Conservative Treatment for Decompensated Cirrhotic Partients With Hepatocellular Carcinoma", World J Gastroenterol, Feb. 15, 2004, vol. 10, No. 4, pp. 505-508.
Chen et al., "Early Response of Hepatocellular Carcinoma to Transcatheter Arterial Chemoembolization: Choline Levels and MR Diffusion Constsants Initial Experience[1]", Radiology, May 2006, vol. 239, No. 2, pp. 448-456.
Adachi et al., "Effects of Preoperative Transcatheter Hepatic Arterial Chemoembolization for Hepatocellular Carcinoma: The Relationship Between Postoperative Course and Tumor Necrosis", Cancer, Dec. 15, 1993, vol. 72, No. 12, pp. 3593-3598.

(Continued)

*Primary Examiner* — Tracy Vivlemore
*Assistant Examiner* — Monica Shin
(74) *Attorney, Agent, or Firm* — Buchanan, Ingersoll & Rooney, PC

(57) ABSTRACT

Disclosed herein is a method for alleviating the condition of spinal canal stenosis, including: transluminally placing a catheter in a lumbar artery, iliolumbar artery or lateral sacral artery at the proximity of a narrowed area of a spinal canal; and injecting a vasodilator into the artery via the catheter.

5 Claims, No Drawings

(56) References Cited

OTHER PUBLICATIONS

Yu et al., "Experience With Liver Resection After Hepatic Arterial Chemoembolization for Hepatocellular Carcinoma" Cancer, Jan. 1, 1993, vol. 71, No. 1, pp. 62-65.
Pacella et al., "Hepatocellular Carcinoma: Long-Term Results of Combined Treatment With Laser Thermal Ablation and Transcatheter Arterial Chemoembolization", Radiology, Jun. 2001, vol. 219, No. 3, pp. 669-678.
Lim et al., "Imaging Features of Hepatocellular Carcinoma After Transcatheter Arterial Chemoembolization and Radiofrequency Ablation", AJR:187, Oct. 2006, pp. W341-W349.
Sakamoto et al., "Intrahepatic Biloma Formation (Bile Duct Necrosis) After Transcatheter Arterial Chemoembolization", AJR:181, Jul. 2003, pp. 79-87.
Kuroda et al., "Limitation of Transcatheter Arterial Chemoembolization Using Iodized Oil for Small Hepatocellular Carcinoma", Cancer, Jan. 1, 1991, vol. 67, pp. 81-86.
Shen et al., "Predictors of Outcome in Patients With Unresectable Hepatocellular Carcinoma Receving Transcatheter Arterial Chemoembolization", 2007(month unknown), The Authors, Aliment Pharmacol Ther 26, pp. 393-400.
Katyal et al., "Prognostic Significance of Arterial Phase CT for Prediction of Response to Transcatheter Arterial Chemoembolization in Unresectable Hepatocellular Carcinoma: A Retrospective Analysis", AJR:175, Dec. 2000, pp. 1665-1672.
Shibata et al., "Small Hepatocellular Carcinoma: Is Radiofrequency Ablation Combined With Transcatheter Arterial Chemoembolization More Effective Than Radiofrequency Ablation Alone for Treatment?", Radiology, Sep. 2009, vol. 252, No. 3, pp. 905-913.
Huang et al., "Survival Benefit of Transcatheter Arterial Chemoembolization in Patients With Hepatocellular Carcinoma Larger Than 10 cm in Diameter", Blackwell Publishing Ltd., Aliment Pharmacol Ther 23, 2006(month unknown), pp. 129-135.
Zhang et al., "The Effect of Preoperative Transcatheter Hepatic Arterial Chemoembolization on Disease-Free Survival After Hepatectomy for Hepatocellular Carcinoma", Cancer, Dec. 15, 2000, vol. 89, No. 12, pp. 2606-2612.
Tanaka et al., "The Long Term Efficacy of Combined Transcatheter Arterial Embolization and Percutaneous Ethanol Injection in the Treatment of Patients With Large Hepatocellular Carcinoma and Cirrhosis", Cancer, Jan. 1, 1998, vol. 82, No. 1, pp. 78-85.
Lee et al., "The Safety and Efficacy of Transcatheter Arterial Chemoembolization in the Treatment of Patients With Hepatocellular Carcinoma and Main Portal Vein Obstruction", Cancer, Jun. 1, 1997, vol. 79, No. 11, pp. 2087-2094.
Lee et al., "Therapeutic Efficacy of Transcatheter Arterial Chemoembolization As Compared With Hepatic Resection in Hepatocellular Carcinoma Patients With Compensated Liver Function in a Hepatitis B Virus-Endemic Area: A Prospective Cohort Study", Journal of Clinical Oncology, Nov. 15, 2002, vol. 20, No. 22, pp. 4459-4465.
Liu et al., "Three-Dimensional Conformal Radiation Therapy for Unresectable Hepatocellular Carcinoma Patients Who Had Failed With or Were Unsuited for Transcatheter Arterial Chemoembolization", Jpn J Clin Oncol, 2004; 34(9), (month unknown) pp. 532-539.
Caturelli et al., "Transcatheter Arterial Chemoembolization for Hepatocellular Carcinoma in Patients With Cirrhosis: Evaluation of Damage to Nontumorous Liver Tissue Long-Term Prospective Study", Radiology, Apr. 2000, vol. 215, No. 1, pp. 123-128.
Chung et al., "Transcatheter Arterial Chemoembolization of Hepatocellular Carcinoma: Prevalence and Causative Factors of Extrahepatic Collateral Arteries in 479 Patients", Korean J Radiol 7(4), Dec. 2006, pp. 257-266.
Minami et al., "Transcatheter Arterial Chemoembolization of Hepatocellular Carcinoma: Usefulness of Coded Phase-Inversion Harmonic Sonography", AJR:180, Mar. 2003, pp. 703-708.
Kim et al., "Transcatheter Arterial Chemoembolization or Chemoinfusion for Unresectable Intrahepatic Cholangiocarcinoma: Clinical Efficacy and Factors Influencing Outcomes", Cancer, Oct. 1, 2008, vol. 113, No. 7, pp. 1614-1622.
Ueno et al., "Transcatheter Arterial Chemoembolization Therapy Using Iodized Oil for Patients With Unresectable Hepatocellular Carcinoma: Evaluation of Three Kinds of Regimens and Analysis of Prognostic Factors", Cancer, Apr. 1, 2000, vol. 88, No. 7, pp. 1574-1581.
Yoon et al., "Transcatheter Arterial Chemoembolization With Paclitaxel-Lipiodol Solution in Rabbit VX2 Liver Tumor", Radiology, Oct. 2003, vol. 229, No. 1, pp.126-131.
Lee et al., "Transcatheter Arterial Chemoembolization for Hepatocellular Carcinoma; Anatomic and Hemodynamic Considerations in the Hepatic Artery and Portal Vein", Radio Graphics 2002 (month unknown); vol. 22, No. 5 pp. 1077-1091.
Sakurai et al., "Transcatheter Chemo-Embolization Effective for Treating Hepatocellular Carcinoma: A Histopathologic Study", Cancer, Aug. 1, 1984, vol. 54, No. 3, pp. 387-392.

* cited by examiner

METHOD FOR ALLEVIATING CONDITION OF SPINAL CANAL STENOSIS BY LOCAL ADMINISTRATION OF MEDICINE

BACKGROUND

1. Technical Field

This invention relates to a method for alleviating the condition of spinal canal stenosis by local administration of a medicine.

2. Description of the Related Art

The respective vertebral bodies ranging from the cervical to sacral spines and internal spaces surrounded by spinous processes are called spinal canal. The spinal canal stenosis means a condition wherein the spinal canal is narrowed such as by the hypertrophic degeneration of the spine making up of the spinal canal and the yellow ligament or by intervertebral disc protrusion, so that the nerve tissues of a nerve root, cauda equine and the like are compressed, thereby causing a variety of symptoms. This spinal canal stenosis may occur ascribed to naturally aged apophysis or from a degenerative disease or condition, or may sometimes occur with the case of a patient who suffers morbid obesity or a patient who takes peroral corticosteroids. Depending on the narrowed (or constricted) site of the spinal canal, the spinal canal stenosis can be classified into cervical spinal canal stenosis, thoracic spinal canal stenosis, lumbar spinal canal stenosis and extensive spinal canal stenosis. As these symptoms, mention is made of low back pain, or upper-extremity or lower-extremity pain or numbness resulting from nerve compression. Especially, if the cauda equinal nerve is damaged, the low back pain, or lower-extremity pain or numbness, or a feeling of weariness becomes severe during walking, and such a symptom is called intermittent claudication.

The treatment method of the spinal canal stenosis is fundamentally carried out according to a conservative medical management that generally, initially makes use of a drug therapy using an analgetic agent, an anti-inflammatory agent or the like, a gymnastic therapy for strengthening the abdominal and back muscles, a thermotherapy using a hot pack, an acupuncture treatment intended for pain relief effect, and an orthotic therapy fitting a corset.

Most of the spinal canal stenoses come to attention of the conservative medical management and many cases have been observed wherein stenotic symptoms are improved by a combination of various conservative therapies. However, a therapeutic medicine that has been accepted for a medical treatment of the spinal canal stenosis is only a prostaglandin E1 derivative preparation intended for an improvement of circulation in nervous system. Although this prostaglandin E1 derivative preparation is now commercially available for oral and intravenous uses, it cannot be said that both are effective against severe spinal canal stenosis involving intermittent claudication. This is considered for the reason that because of systemic administration, the local blood circulation at a stenotic site cannot be effectively improved. Such systemic administration involves such side effects to promote hemorrhage of patients having bleeding disorders such as, for example, intracranial bleeding, gastrointestinal bleeding, blood spitting and the like. A full recovery with the help of the conservative medical therapy is rare and such a therapy has often ended up in vain.

Especially, with the case of severely ill patients, decompressive laminectomy wherein the patients are subjected to spinal and nerve root decompressions is carried out. In this therapy, the back and muscles are cut open to remove the support structure from the backbone thereby exposing a rear face of the spine, followed by removing the vertebral arch portion covering the back side of the spinal canal to expose a thickened yellow ligament (laminectomy). Subsequently, the ligament of the thickened yellow ligament is removed. This treatment is carried out under general anesthesia. The patient generally needs to be hospitalized over about five to seven days depending on the age and general conditions of the patient, and it should take six weeks to three months before recovery from the treatment. Additionally, most of the patients have to be extended in treatment at rehabilitation facility so as to regain enough motion to live alone, thereby imposing a substantial burden on patient.

As set out above, in spite of the fact that the spinal canal stenosis causes many distressing symptoms on the part of patient, effective treatments and symptom-alleviating methods have never been established yet.

SUMMARY

Accordingly, it is an object of the invention to provide a method for alleviating the condition of spinal canal stenosis or treating the spinal canal stenosis, wherein patient burden is reduced.

Another object of the invention is to provide a method for alleviating the condition of spinal canal stenosis or treating the spinal canal stenosis, wherein side effects can be reduced.

In accordance with one embodiment, there is provided a method for alleviating the condition of spinal canal stenosis, which includes:

transluminally placing a catheter in a lumbar artery, iliolumbar artery or lateral sacral artery at the proximity of a narrowed area of a spinal canal; and injecting a vasodilator into the artery via the catheter.

According to the method of the invention, the condition of the spinal canal stenosis can be alleviated, or the spinal canal stenosis can be treated in a state of reducing patient burden.

The above and other objects, features and advantages of the present invention will become clear from the following description of the preferred embodiments.

DETAILED DESCRIPTION OF THE PREFERRED EMBODIMENT

The invention is concerned with a method for alleviating the condition of spinal canal stenosis, which includes:

(i) transluminally placing a catheter in a lumbar artery, iliolumbar artery or lateral sacral artery at the proximity of a narrowed area of a spinal canal (hereinafter referred to simply as "target area") (step (i)); and (ii) injecting a vasodilator into the artery via the catheter (step (ii)). More specifically, the method of the invention is one wherein a catheter is transluminally delivered to an artery proximal to a narrowed area of the spinal canal, and antegradely administering a medicine therefrom.

As stated hereinbefore, prostaglandin E1 derivative preparation has been hitherto systemically administered as a conservative medical management of spinal canal stenosis for the purpose of improving the circulation in nervous system. However, because of the systemic administration, high dose cannot be used, so that a satisfactory effect cannot be expected or complete recovery is difficult in most cases. In addition, such a method has a problem in that the medicine acts not only on the narrowed area, but also on normal tissues, for which when it is administered over a long term, the side effect of the medicine is liable to be induced, e.g. with patients having a bleeding disorder such as, for example, intracranial bleeding, alimentary canal bleeding or blood spitting, and the like, bleeding is apt to be induced.

In contrast thereto, according to the method of the invention, a vasodilator is locally injected into the narrowed area from the vicinity of the area of the spinal canal via a catheter, so that the medicinal effect can be selectively shown from the narrowed area over the periphery. Since no surgical operation is employed in the method of the invention, patient burden is much reduced (i.e. minimally invasive). Thus, according to the method of the invention, there are the following advantages: (a) the spinal canal stenosis can be effectively treated or the condition of spinal canal stenosis can be effectively alleviated; (b) the side effects ascribed to vasodilator can be significantly reduced; and (c) this method is a minimally invasive method wherein patient burden is low. The method of the invention is particularly effective for severe spinal canal stenosis.

Preferred embodiments of the invention are now described.

Initially, in the step (i), a catheter is transluminally set up in the lumbar artery or iliolumbar artery or lateral sacral artery at the proximity of a narrowed area of the spinal canal. Although the artery to be set up with the catheter is the lumbar artery, iliolumbar artery or lateral sacral artery, it is preferred to select the artery that is located most closely to the narrowed area of the spinal canal. In doing so, it becomes possible to more selectively, locally inject a vasodilator to the narrowed area of the spinal canal thereby enabling the vasodilator to be more effectively acted over from the target area to the periphery. It will be noted that to place a catheter in whichever artery chosen among the above-mentioned arteries can be confirmed according to a known technique, and it is preferred to select an artery that is close to the narrowed area of the spinal canal. For instance, there is favorably employed a method such as of carrying out the operations by use of an X-ray.

The catheter used in the invention is not particularly limited and is appropriately selected depending on the diameter of an artery to which a catheter is introduced and the branching mode of the artery. More particularly, known respiratory, cardiovascular and gastrointestinal catheters used in medical fields, particularly, catheters ordinarily used upon administration of a medicine in a blood vessel, can be used in a similar way or after appropriate modification. For instance, mention is made of a microcatheter, an infusion catheter, a perfusion catheter and the like. The structure of the catheter is also not particularly limited and, for example, with respect to the number of lumens, thickness, length and the presence or absence of balloon, a clinician appropriately determines them while taking the ease in transportation to a target area and the thickness of an artery at the target area into consideration.

For example, there is used a catheter that has openings at a distal side and also at a proximal side and is provided with a lumen capable of sending a solution to the distal side. The catheter used may be a commercially available one, and there are used, for example, a microcatheter for intravascular procedure and diagnosis responsive to diagnosis and treatment of fine blood vessels such as in liver (e.g. Progreat (registered trade name), made by Terumo Corporation), a microcatheter for narrowed area passage used to pass a guide wire through intravascular lumen stenosis in the cardiovascular area (e.g. FINECROSS (registered trade name), made by Terumo Corporation), and the like.

In the step (i), a catheter inserting site is not particularly limited and a catheter may be applied to an ordinary catheter inserting site such as of the femoral artery, brachial artery, radial artery or the like. For the insertion of a catheter, it may be inserted into a target area via a separate guide wire or guiding catheter. According to one embodiment, a sheath is placed in main artery, and a guide wire is inserted initially through this sheath into the vicinity of a target area under X-ray fluoroscopy. Next, this guide wire is placed in one lumen of the guiding catheter to permit the tip of the guiding catheter to be located at a site upstream of the target area, e.g. at an inlet of the lumbar artery. Moreover, the guide wire is withdrawn and the tip of the catheter is induced to the target area through the lumen of the guiding catheter. Alternatively, the guide wire may be inserted into the lumen of a microcatheter to induce the tip of the catheter to the target area through the guide wire. According to such an operation as set out above, the tip of the microcatheter is transluminally placed in the lumbar artery, iliolumbar artery or lateral sacral artery at the proximity of the narrowed area of the spinal canal. In this embodiment, a balloon may be set up at the tip of the guiding catheter or microcatheter. In this way, the catheter can be readily introduced to a desired site as entrained with a blood flow.

Whether the catheter tip is placed at a desired position can be confirmed by a contrast agent contained in the shaft of the catheter or by means of the guide wire. Alternatively, a contrast agent or a physiological saline solution containing a contrast agent may be flown from the tip of the catheter. This permits the position of the tip of the catheter to be more exactly confirmed, so that the vasodilator can be more effectively acted on the target area. More specifically, it is preferred that the method of the invention further includes, prior to the injection of a vasodilator into the lumbar artery, iliolumbar artery or lateral sacral artery, injecting a contrast agent through the catheter to confirm the contrast agent being flown from the catheter into the above-indicated artery. The contrast agent used is not particularly limited and known contrast agents may be used. For instance, mention is made of a nonionic water-soluble iodine contrast agent, a water-soluble iodine contrast agent, a low osmotic pressure water-soluble iodine contrast agent and the like. The injection amount of the contrast agent may be at a level sufficient for confirming that the catheter is placed in a desired artery. In general, the injection amount of the contrast agent may be at about 1 to 10 mL.

Next, in the step (ii), the vasodilator is injected into the above-indicated artery through the catheter. More particularly, a syringe having a vasodilator contained therein is connected to a hub at the base end portion of the catheter and the vasodilator is injected from the tip of the catheter into the artery. It will be noted that a three-way stopcock may be provided between the hub at the base end portion of the catheter and the syringe. Alternatively, an infusion bag containing a vasodilator may be connected to the hub at the base end portion of the catheter, followed by injecting the vasodilator into a target area by means of a pump. This allows the vasodilator to be slowly injected at a given injection rate.

On this occasion, the distance between the tip portion of the catheter from which the vasodilator is injected and the spinal artery at a more peripheral side corresponding to the area where the spinal canal is narrowed is very short. The vasodilator is selectively, preferentially injected into the spinal artery corresponding to the narrowed area of the spinal canal, so that the vasodilator acts on from the narrowed area of the spinal canal to the periphery with its medicinal effect being effectively shown. Accordingly, the patient, subjected to treatment according to the method of the invention, is locally administered with a vasodilator at the area where the spinal canal is narrowed. Therefore, a treatment effect on the spinal canal stenosis or an effect of alleviating the condition of the spinal canal stenosis becomes very high and the adverse effect is low. Additionally, the method of the invention makes use of catheters and needs no surgical operation, so that patient burden is reduced.

The vasodilators used are not particularly limited and can be appropriately selected depending on the type and seriousness of spinal canal stenosis and the condition of patient. More particularly, mention is made, for example, of prostaglandins, prostaglandin derivative preparations, nonsteroidal anti-inflammatory drugs (NSAID), steroidal anti-inflammatory drugs, antiplatelet drugs, vitamins, muscle relaxant drugs, antidepressant drugs, poly ADP-ribose polymerase (PARP) inhibitors, excitatory amino acid receptor antagonists, radical scavengers, astrocytic function improvers, IL-8 receptor antagonists, immunosuppressive drugs, aldose reductase inhibitors, phosphodiesterase (PDE) inhibitors, and nitrogen monoxide synthetic enzyme inhibitors. Of these, prostaglandins, prostaglandin derivative preparations, nonsteroidal anti-inflammatory drugs (NSAID), steroidal anti-inflammatory drugs, antiplatelet drugs, vitamins, muscle relaxant drugs, antidepressant drugs, poly ADP-ribose polymerase (PARP) inhibitors, excitatory amino acid receptor antagonists, radical scavengers, astrocytic function improvers, IL-8 receptor antagonists and immunosuppressive drugs are preferred.

Although not limited to those indicated below, prostaglandins include, for example, prostaglandin $A_1$, prostaglandin $A_2$, prostaglandin $A_3$, prostaglandin $B_1$, prostaglandin $B_2$, prostaglandin $B_3$, prostaglandin $C_1$, prostaglandin $C_2$, prostaglandin $C_3$, prostaglandin $D_1$, prostaglandin $D_2$, prostaglandin $D_3$, prostaglandin $E_1$, prostaglandin $E_2$, 8-isoprostaglandin $E_2$, prostaglandin $E_3$, prostaglandin $F_{1\alpha}$, prostaglandin $F_{2\alpha}$, 13,14-dihydro-15-keto-prostaglandin $F_{2\alpha}$, 8-isoprostaglandin $F_{2\alpha}$, 8-iso-13,14-dihydro-15-keto-prostaglandin $F_{2\alpha}$, 8-epiprostaglandin $F_{2\alpha}$, prostaglandin $F_{3\alpha}$, prostaglandin $F_{1\beta}$, prostaglandin $F_{2\beta}$, prostaglandin $F_{3\beta}$, prostaglandin $G_1$, prostaglandin $G_2$, prostaglandin $G_3$, prostaglandin $H_1$, prostaglandin $H_2$, prostaglandin $H_3$, prostaglandin $I_1$, prostaglandin $I_2$, prostaglandin $I_3$, prostaglandin $J_2$, 6-keto-prostaglandin $F_{1\alpha}$, 2,3-dinor-6-keto-prostaglandin $F_{1\alpha}$, 13,14-dihydro-15-keto-prostaglandin $E_2$, 7α-hydroxy-5,11-diketo-tetranor-prosta-1,16-dioic acid, 5α,7α-dihydroxy-11-keto-tetranor-prosta-1,16-dioic acid and the like. The above prostaglandins may be used in the form as it is or in the form of a free base or in the form of a salt. Although not limited to those indicated below, the prostaglandin salts include, for example, salts of alkali metals (e.g. potassium, sodium and the like), salts of alkaline earth metals (e.g. calcium, magnesium and the like), ammonium salts, pharmaceutically acceptable organic amines (e.g. tetramethylammonium, triethylamine, methylamine, dimethylamine, cyclopentylamine, benzylamine, phenethylamine, piperidine, monoethanolamine, diethanolamine, tris (hydroxymethyl) aminomethane, lysine, arginine, N-methyl-D-glucamine and the like), and acid addition salts (e.g. inorganic acid salts such as hydrochloride salts, hydrobromate salts, hydroiodide salts, sulfate salts, phosphate salts and nitrate salts; and organic acid salts such as acetate salts, lactate salts, tartrate salts, benzoate salts, citrate salts, methanesulfonate salts, ethanesulfonate salts, benzene sulfonate salts, toluene sulfonate salts, salts of isethionic acid, salts of glucuronic acid and gluconate salts).

Although not limited to those indicated below, prostaglandin derivative preparations include, for example, alprostadil, ornoprostil, limaprost, gemeprost, beraprost, trimoprostil, misoprostol, arbaprostil, enprostil or the like.

Although not limited to those indicated below, nonsteroidal anti-inflammatory drugs (NSAID) include, for example, sasapyrine, sodium salicylate, aspirin, aspirin-dialuminate formulation, diflunisal, indomethacin, suprofen, ufenamate, dimethylisopropyl azulene, bufexamac, felbinac, diclofenac, tolmetin sodium, clinoril, fenbufen, nabumetone, proglumetacine, indometacin farnesil, acemetacin, proglumetacin maleate, amfenac sodium, mofezolac, etodolac, ibuprofen, ibuprofen piconol, naproxen, flurbiprofen, flurbiprofen axetil, ketoprofen, fenoprofen calcium, tiaprofen, oxaprozin, pranoprofen, loxoprofen sodium, alminoprofen, zaltoprofen, mefenamic acid, mefenamic acid aluminum, tolfenamic acid, floctafenine, ketophenylbutazone, oxyphenbutazone, piroxicam, tenoxicam, ampiroxicam, napageln ointment, epirizole, tiaramide hydrochloride, tinoridine hydrochloride, emorfazone, sulpyrine, migrenin, thalidone, sedes G, amipylo-N, sorbon, pyrine cold remedies, acetaminophen, phenacetin, dimetotiazine mesilate, simetride formulation, non-pyrine cold remedies and the like.

Although not limited to those indicated below, the antiplatelet drugs include, for example, aspirin, ticlopidine, ticlopidine hydrochloride, clopidogrel, dipyridamole, cilostazol, ozagrel, ozagrel sodium, prasugrel, ethyl icosapentate, beraprost, sarpogrelate, sarpogrelate hydrochloride, limaprost, GPIIb/IIIa receptor antagonists (e.g. abciximab, tirofiban, eptifibatide, YM028 and the like), AZD6140, beraprost sodium and the like.

Although not limited to those indicated below, vitamins include, for example, vitamin $B_1$, vitamin $B_{12}$ and the like.

Although not limited to those indicated below, the muscle relaxant drugs include, for example, tolperisone hydrochloride, chlorzoxazone, chlormezanone, methocarbamol, phenprobamate, pridinol mesylate, chlorphenesin carbamate, baclofen, eperisone hydrochloride, afloqualone, tizanidine hydrochloride, alcuronium chloride, suxamethonium chloride, tubocurarine chloride, dantrolene sodium, pancuronium bromide, vecuronium bromide and the like.

Although not limited to those indicated below, the antidepressant drugs include, for example, tricyclic antidepressant drugs such as imipramine hydrochloride, desipramine hydrochloride, clomipramine hydrochloride, trimipramine maleate, amitriptyline hydrochloride, nortriptyline hydrochloride, lofepramine hydrochloride, amoxapine, dosulepin hydrochloride and the like, and tetracyclic antidepressant drugs such as maprotiline, mianserin and the like.

Although the poly ADP-ribose polymerase (PARP) inhibitors are not limited to those indicated below, mention is made, for example, of 1,5-dihydroxyisoquinoline and the like.

Although not limited to those indicated below, the excitatory amino acid receptor antagonists include, for example, an NMDA receptor antagonist, an AMPA receptor antagonist and the like.

Although not limited to those indicated below, the radical scavengers include, for example, edaravone, ebselen (DR-3305) and the like.

Although not limited to those indicated below, the astrocytic function improvers include, for example, ONO-2506 and the like.

A known IL-8 receptor antagonist can be used as an IL-8 receptor antagonist although not limited thereto.

Although not limited to those indicated below, the immunosuppressive drugs include, for example, cyclosporine, FK506 and the like.

Although not limited to those indicated below, the aldose reductase inhibitors include, for example, epalrestat, fidarestat, AS-3201, zenarestat, imirestat, AL-4114, ICI-10552, ICI-215918, ZD-5522, BAL-ARI8, methosorbinil, FR-62765, WF-2421, GP-1447, IDD-598, JTT-811, ADN-138, ADN-311, lindolrestat, SG-210, M-16049, M-16209, NZ-314, sorbinil, zopolrestat, CP-AR-3192, ascorbyl gamolenate, risarestat, salfredins, AD-5467, TJN-732, TAT, tolrestat, thiazocin-A, axillarin, ICI-215918, ponalrestat, minalrestat, DN-108, SPR-210, A-74863a and the like.

Although not limited to those indicated below, the phosphoesterase (PDE) inhibitors include, for example, a PDE3 inhibitor, a PDE4 inhibitor, a PDE5 inhibitor and the like. The PDE3 inhibitor includes, for example, amrinone, milrinone, vesnarinone, cilostazol, sildenafil or the like. The PDE4 inhibitor includes, for example, cilomilast (commercial name: Ariflo), Roflumilast (BY-217), Arofylline, OPC-6535, ONO-6126, 10-485, AWD-12-281, CC-10004, CC-1088, KW-4490, Iirimilast, ZK-117137, YM-976, BY-61-9987, CC-7085, CDC-998, MEM-1414, ND-1251, Bay19-8004, D-4396, PD-168787, Atizoram (CP-80633), Cipamfylline (BRL-61063), Rolipram, NIK-616, SCH-351591, V-11294A or the like. The PDE5 inhibitor includes, for example, Sildenafil or Sildenafil citrate. As other PDE inhibitor, mention is made, for example, of NT-702 and the like.

Although not limited to those indicated below, nitrogen monoxide synthetic enzyme inhibitors include, for example, $N^\omega$-monomethyl-L-arginine (L-NMMA), $N^\omega$-nitro-L-arginine (L-NNA), $N^\omega$-nitro-L-arginine methyl ester (L-NAME), $N^\omega$-amino-L-arginine (L-NAA), $N^\omega$-cyclopropyl-L-arginine (L-CPA), $N^\omega$-allyl-L-arginine (L-ALA), $N^\omega$-nitro-L-arginine-p-nitroanilide, $N^\omega,N^\omega$-dimethylarginine, 2-iminobiotin, S-methyl-L-thiocitrulline, S-ethyl-L-thiocitrulline, L-thiocitrulline, L-homothiocitrulline, 2-iminopiperidine, 2-iminohomopiperidine, S-methylisothiourea, S-ethylisothiourea (EIT), S-isopropylisothiourea, S,S'-(1,3-phenylenebis(1,2-ethanediyl))bisisothiourea, 2-aminothiazoline, 2-aminothiazole, N-(3-(aminomethyl)benzyl)-acetamidine, $N^\delta$-(4,5-dihydrothiazol-2-yl)ornithine, $N^\omega$-iminoethyl-ornithine (L-NIO), L-$N^6$-(1-iminoethyl)-lysine, 2-amino-5,6-dihydro-6-methyl-4H-1,3-thiazine (AMT), or (+)-trans-3-imino-5-methyl-7-chloro-2-azabicyclo[4.1.0]heptane.

The above vasodilators may be used singly or in combination of two or more. It is preferred that an effective component of the vasodilator can be supplied in such a way as to be continuously supplied to a disease site. To this end, the vasodilator is preferably injected into the lumbar artery or iliolumbar artery or lateral sacral artery in the form of a sustained-release preparation. Although not limited to specific ones, the sustained-release preparations include, for example, sustained-release injectable drugs such as a microcapsule preparation, a microsphere preparation, a nanosphere preparation and the like. Although the sustained-release preparation is not specifically limited and ordinarily employed sustained-release injectable drugs can be used, sustained-release injectable drugs in the form of microcapsule, microsphere or nanosphere preparations are preferred. The microcapsule preparation, microsphere preparation and nanosphere preparation used herein mean a preparation that contains such a vasodilator (effective component) as set out above as an active ingredient and is in the form of microparticles along with a bioabsorbable or biodegradable polymer.

According to the drug sustained-release system making use of such a sustained-release preparation, a vasodilator can be acted on the narrowed area of the spinal canal over a long time. In the drug sustained-release systems, there are some systems making use of a bioabsorbable or biodegradable polymer wherein natural polymers or synthetic polymers are used therefor. For the control mechanism of a sustained-release rate, there are known a degradation control type, a diffusion control type and a membrane transmission control type.

Although not limited to those indicated below, natural polymers serving as a bioabsorbable polymer include, for example, plant-derived polysaccharides (e.g. cellulose, starch, alginic acid and the like), animal-derived polysaccharides and proteins (e.g. chitin, chitosan, collagen, gelatin, albumin, glucosaminoglucane and the like), microorganism-producing polyesters and polysaccharides (e.g. poly-3-hydroxyalkanoate, hyaluronic acid and the like).

Although not limited to those indicated below, the biodegradable polymers include, for example, fatty acid ester polymers or copolymers, polyacrylic acid esters, polyhydroxybutyric acids, polyalkylene oxalates, polyorthoesters, polycarbonates and polyamino acids, which may be used singly or in admixture. The fatty acid ester polymers or copolymers thereof include polylactic acid, polyglycolic acid, polycitric acid, polymalic acid, polyethylene succinate, polybutylene succinate, poly-ε-caprolactone, polybutylene terephthalate/adipate or lactic acid-glycolic acid copolymer, which may be used singly or in admixture. Besides, there may be used one or more of poly-α-cyanoacrylic acid ester, poly-β-hydroxybutyric acid, polytrimethylene oxalate, poly-orthoester, polyorthocarbonate, polyethylene carbonate, poly-γ-benzyl-L-glutamic acid, polyvinyl alcohol, polyester carbonate, polyacid anhydride, polycyano acrylate, polyphosphazene or poly-L-alanine. Preferably, polylactic acid, polyglycolic acid or lactic acid-glycolic acid copolymer is mentioned, of which lactic acid-glycolic acid copolymer is more preferred. The average molecular weight of the biodegradable high-molecular polymer is preferably from about 2,000 to about 800,000, more preferably from about 5,000 to about 200,000. For instance, with polylactic acid, one having a weight average molecular weight ranging from about 5,000 to about 100,000 is preferred. More preferably, it ranges from about 6,000 to about 50,000. Polylactic acid can be prepared according to a preparation process known per se. In the lactic acid-glycolic acid copolymer, the compositional ratio between lactic acid and glycolic acid is preferably from about 100/0 to about 50/50 (ratio by weight), more preferably from about 90/10 to 50/50 (ratio by weight). The weight average molecular weight of the lactic acid-glycolic acid copolymer is from about 5,000 to about 100,000. More preferably, it ranges from about 10,000 to 80,000. The lactic acid-glycolic acid copolymer can be prepared according to a known preparation process. In order to suppress an initial burst, basic amino acids (e.g. alginic acid and the like) may be added. It will be noted that in the present specification, the weight average molecular weight means a molecular weight that is measured by gel permeation chromatography (GPC) as converted to polystyrene. In so far as the purpose of the invention can be achieved, the biodegradable high molecular polymer can be changed depending on the intensity of pharmacological activity of an effective component and the intended drug release, and is used in an amount, for example, of about 0.2 to about 10,000 times (ratio by weight) for the vasodilator, preferably about 1 to about 1,000 times (ratio by weight) and more preferably about 1 to about 100 times (ratio by weight).

The method of preparing microspheres, microcapsules or nanospheres is not particularly limited, for which a known method as described, for example, in Japanese Patent Laid-open No. 2010-120964 is applied thereto in a similar way or after appropriate modification. More particularly, mention is made of a drying-in-water method (e.g. an o/w method, a w/o method, a w/o/w method or the like), a phase separation method, a spray-drying method, a granulation method using a supercritical fluid or a method similar thereto.

Further, the method of converting a sustained-release preparation to a sustained-release injectable drug is not particularly limited, for which there can be applied a method described, for example, in Japanese Patent Laid-open No.

2010-120964 in a similar way or after appropriate modification. For instance, in order to provide microspheres as an injectable drug, microspheres are converted to an aqueous suspension along with a dispersant, a preservative, a tonicity agent, a buffer agent and a pH adjuster thereby obtaining an injectable preparation of practical use. Moreover, practically usable injectable drugs may also be provided by dispersing the microspheres along with a plant oil or its mixture with a phospholipid such as lecithin, or along with a medium-chain triglyceride (e.g. Miglyol 812 or the like) to provide oil suspensions. The particle size of the microspheres is not specifically limited and may be, for example, within a range satisfying the dispersity and the ease in passage through needle in case where they are applied to as an suspension for injection. The average particle size of the microspheres is preferably at about 0.1 to about 300 μm, more preferably at about 1 to about 150 μm, and much more preferably at about 2 to about 100 μm. In order to provide microspheres as an aseptic preparation, mention is made of a method wherein all the preparation steps are made aseptically, a method of sterilization with a γ-ray, and a method of adding an antiseptic although not limited thereto.

In the practice of the invention, although the dose of a vasodilator can be appropriately selected depending on the type and form of vasodilator, the duration time of drug release, the type and seriousness of spinal canal stenosis, and the condition of patient, it may be an effective amount of a vasodilator. In general, one dosage of a vasodilator is at about 0.5 to 10 μg, preferably at about 1 to 5 μg, per adult (body weight of 50 kg). The vasodilator in such an amount can be continuously administered over 1 to 30 minutes in every administration.

Such a method as set out above is a method wherein a vasodilator is locally injected from the vicinity of the narrowed area of the spinal canal through a catheter to the narrowed area. Hence, the vasodilator can be selectively and locally acted on the narrowed area. Therefore, according to the method, the spinal canal stenosis can be effectively treated or the condition of the spinal canal stenosis can be effectively alleviated. The method of the invention involves no surgical operations, so that patient burden is much reduced (i.e. minimally invasive)

EXAMPLE

A method wherein a catheter is transluminally delivered to the artery proximal to a narrowed area of the spinal canal, for which a drug is antegradely administered is described in detail based on a preferred embodiment. In this regard, however, it should be construed that the technical range of the invention is not limited only to the example.

Example 1

Using a catheter introducer kit (Radifocus Introducer, made by Terumo Corporation), a sheath is placed in the crural artery of a patient. Next, a guide wire (Radifocus Guide Wire M, made by Terumo Corporation) is inserted from the sheath and the tip of the guide wire is forced from the crural artery into the abdominal aorta under X-ray fluoroscopy, followed by further forcing from the abdominal aorta to the lumbar artery. A guiding catheter (catheter M for Radifocus Angiography, made by Terumo Corporation) is inserted along the guide wire and the tip of the catheter is placed at an inlet of the lumbar artery while confirming it under X-ray fluoroscopy. After confirmation of the tip of the catheter being placed in desired position, the guide wire is withdrawn.

Subsequently, a microcatheter (Progreat, made by Terumo Corporation) is inserted into the guiding catheter and the tip of the catheter is pushed forward through the lumbar artery to an extent most closely to the narrowed spinal artery. At this stage, a small amount of a contrast agent is slowly injected by means of a syringe, whereupon the flow of the contrast agent form the tip of the microcatheter into the lumbar artery is confirmed.

A syringe of prostaglandin E1 preparation for intravenous injection (PRINK Inj. Syringe, made by Kaken Pharmaceutical Co., Ltd.) is inserted into a catheter hub at the terminal end of the microcatheter and 0.5 mL (2.5 μg of alprostadil), of an injectable drug is slowly injected at a rate of 50 μL/min. After full injection of 0.5 mL of the injectable drug, the microcatheter and guiding catheter are withdrawn, followed by hemostasis of the crural artery.

What is claimed is:

1. A method for alleviating the condition of spinal canal stenosis, comprising:
    selecting an artery from among a lumbar artery, iliolumbar artery and lateral sacral artery that is located closest to a narrowed area of a spinal canal;
    transluminally placing a catheter in the selected artery; and
    injecting a vasodilator into the selected artery via the catheter.

2. The method as defined in claim 1, further comprising injecting, prior to injection of the vasodilator into the lumbar artery, iliolumbar artery or lateral sacral artery, a contrast agent through the catheter into the artery, and confirming that the contrast agent is flown from the catheter into the artery.

3. The method as defined in claim 1, wherein said vasodilator is at least one selected from the group consisting of a prostaglandin, a prostaglandin derivative preparation, a non-steroidal anti-inflammatory drug (NSAID), a steroidal anti-inflammatory drug, an antiplatelet drug, a vitamin, a muscle relaxant drug, an antidepressant drug, a poly ADP-ribose polymerase (PARP) inhibitor, an excitatory amino acid receptor antagonist, a radical scavenger, an astrocytic function improver, an IL-8 receptor antagonist, and an immunosuppressive drug.

4. The method as defined in claim 1, wherein said vasodilator is injected, in the form of a sustained-release preparation, into the lumbar artery, iliolumbar artery or lateral sacral artery.

5. The method as defined in claim 4, wherein said sustained-release preparation is a sustained-release injectable drug in the form of microcapsules, microspheres or nanospheres.

* * * * *